United States Patent [19]

Sulc et al.

[11] Patent Number: 4,696,974
[45] Date of Patent: Sep. 29, 1987

[54] HYDROPHILIC SILICONE COMPOSITE AND THE METHOD FOR PRODUCING THEREOF

[75] Inventors: Jirí Sulc; Petr Vondrácek; Petr Lopour, all of Praha, Czechoslovakia

[73] Assignee: Ceskoslevenska Akademie Ved, Czechoslovakia

[21] Appl. No.: 862,675

[22] Filed: May 13, 1986

[30] Foreign Application Priority Data

May 20, 1985 [CS] Czechoslovakia ............ 3599-85

[51] Int. Cl.$^4$ ............................................. C08L 83/04
[52] U.S. Cl. .................................... 525/92; 525/100; 523/105; 523/113
[58] Field of Search ................................ 525/92, 100

[56] References Cited

U.S. PATENT DOCUMENTS 3,627,836 11/1968 Getson ........................... 525/100
4,230,826 10/1980 Sommer et al. ................. 525/100
4,616,064 10/1986 Zukosky et al. ................. 525/92

Primary Examiner—Lewis T. Jacobs
Attorney, Agent, or Firm—Leydig, Voit & Mayer

[57] ABSTRACT

Hydrophilic silicones composite contain 10 to 150 wt. parts of a powdered hydrogel filler with particle size $10^{-6}$ to $10^{-1}$ mm on 100 parts by weight of crosslinked silicone polymer which forms a continuous matrix of the composite. The used hydrogel filler is formed made of physically or chemically crosslinked polymers or copolymers of polyol or dihydroxyether monomethacrylates, amides of methacrylic or acrylic acid or their N-monosubstituted and N,N-disubstituted derivatives, or a multiblock copolymer of acrylonitrile with acrylamide and/or acrylic acid. The hydrogel filler is mixed into the non-crosslinked silicone rubber, which is, after shaping, crosslinked by the known procedure of silicone rubber vulcanization at temperatures ranging from 15° to 200° C. These composites are substantially stronger, more plastic, and absorb more water than expected. Tensile strength and shape memory are improved. The composites are useful as biomaterials.

3 Claims, No Drawings

HYDROPHILIC SILICONE COMPOSITE AND THE METHOD FOR PRODUCING THEREOF

BACKGROUND

Hydrophilic silicone elastomers known so far are prepared by grafting of hydrophilic monomers directly on the surface or in the bulk of silicone elastomers as it is described by B. D. Ratner and A. S. Hoffman in "Radiation grafted hydrogels on silicon rubber as new biomaterials" in the book "Biomedical Applications of Polymers" (H. P. Gregor, ed.), Plenum Publishing Corp., New York. In this way, a homogenous hydrogel—silicon rubber material is obtained. However, the grafting was successful only with the mixture of N-vinylpyrrolidone and 2-hydroxyethyl methacrylate (HEMA), whereas HEMA alone gave only a surface grafted silicone rubber. Highest grafting was attained in an aqueous medium first if N-vinylpyrrolidone exceeded HEMA in volume. This homogeneous grafting changes the suitable properties of silicone rubber in the undesirable way.

Moreover, it is known that the plasticized PVC or also synthetic butadiene—acrylonitrile rubber may be filled with powdered synthetic hydrogels, as synthetic ion exchangers or relatively high crosslinked poly(2-hydroxyethyl methacrylate) (poly-HEMA), in the production of thin-walled articles, e.g. artificial leathers or impregnated fabrics. The reason and the result of the addition of powdered hydrophilic polymers was the enhanced permeability of water vapour in these polymers; see, for example, U.S. Pat. Nos. 3,875.261 and 3,928.704 (V. Heidingsfeld et al.). U.S. Pat. No. 4,228.205 (S. Hedecek et al.). In contrast to the above mentioned grafted silicon elastomers, the materials based on plasticized PVC and synthetic rubber were not applicable for medical purposes but only in the production of shoes, gloves, and protective apparels.

SUMMARY OF THE INVENTION

It has been found that silicone elastomers filled with powdered hydrophilic polymers according to the present invention have very suitable properties for applications as biomaterials. The hydrophilic silicone composite according to the invention contains 10 to 150 wt. parts of powdered hydrophilic filler with particle size $10^{-6}$ to $10^{-1}$ mm in 100 parts of the crosslinked silicone polymer which forms a continuous matrix of the composite, whereas the hydrogel filler used is formed by particles of a polymeric hydrogel based on physically or chemically crosslinked polymers or copolymers of polyol or dihydroxyether monomethacrylates, amides of methacrylic or acrylic acid or their N-substituted and N,N-disubstituted derivatives, or a multiblock copolymer of acrylonitrile with acrylamide or acrylic acid. We have found, for example, that the strength of dry composites is substantially higher than their strength in a water-swollen state and that the elastic elongation is much higher than that of the hydrogel alone. At the same time, the swelling capacity in water and in other solvents, as ethanol or ethylene glycol monoethyl ether, is higher than corresponds to the content of hydrogel in the composite. Tensile strength is also lowered by addition of the swollen hydrogel substantially less than would correspond to the content of silicone rubber in the composite. Besides this, the non-swollen composite has the shape memory at a temperature above $T_g$ of the hydrogel. If the composite is strained in the dry state at a temperature above 100° C. and cooled in the deformed state, its shape is very stable at normal and slightly higher temperatures. However, it resumes the original shape before straining by heating above 100° C. or swelling in a suitable solvent, for example, water or ethanol. This can be employed, for example, for introducing some body of complex shape into a living organism. The silicon composite can be also used for stiffening the extension of incompletely closing vocal chords or other organs. The compensation of missing tissues in plastic surgery is facilitated by utilizing the shape memory in connection with swelling.

It is quite striking that the heterogeneous material with a two-phase structure has much better physicochemical properties than the materials having the same chemical composition in total but a homogeneous structure mentioned in the first paragraph of this description. The water-swollen material has higher strength and elastic elongation than the homogeneous unfilled silicone rubber vulcanizate.

An advantageous method of production of shaped bodies from biomaterials consists in the thorough mixing of non-vulcanized silicone rubber with the hydrophilic powdered filler, addition of a vulcanizing agent, e.g. organic peroxide, and press-moulding of the article at a higher temperature with vulcanization same time. Articles from the composites of silicone rubber and powdered hydrogel can be prepared also with the room temperature vulcanizing silicone rubber vulcanizable at normal temperature. In this case, the silicone rubber is mixed with the respective crosslinking agent and with the powdered hydrogel, the mixture is pressed into a mould and allowed to cure. In bodies made from the composites in question, the silicone elastomer forms an elastic and virtually hydrophobic matrix which contains the filler dispersed in such a way that its individual particles are accessible to water or other swelling agent from outside either directly or indirectly. Provided that this material contains at least 10% of the hydrophilic filler, it is suitable, besides for foils, also for the production of thick-walled bodies.

The powdered hydrophilic filler is prepared, for example, by a precipitation polymerization of 2-hydroxyethyl methacrylate (HEMA) in toluene or in another liquid which dissolves the monomer but does not dissolve the polymer, or by grinding the non-swollen large particles or blocks of poly-HEMA. The polymerization is carried out in the presence of a crosslinking agent, in this case of ethylene dimethacrylate, advantageously in the amount larger than is used in the production of contact lenses but smaller than is usually applied in the production of sorbents or cast masses for stomatology, i.e. in the amount of about 1 to 3% on the weight of HEMA. Another suitable hydrophilic filler is polyacrylamide crosslinked with 1 to 3% of methylenebis(-methacrylamide) or other suitable crosslinking agent. If it is desirable to use the hydrogel with higher content of water in the equilibrium-swollen state, multiblock copolymers of acrylonitrile with acrylamide or acrylic acid are very suitable, which are prepared by the controlled partial hydrolysis of polyacrylonitrile in concentrated nitric acid or in 70 to 85% sulfuric acid, or in alkalized solutions of polyacrylonitrile in concentrated aqueous or alcoholic solutions of sodium sulfocyanide. As other hydrogels may serve copolymers of N-vinylpyrrolidone with esters of acrylic or methacrylic acid and lower aliphatic alcohols, for example, with methyl methacrylate, having also a multiblock structure.

The multiblock copolymers of both above mentioned types may be also used in the uncrosslinked state as they are completely insoluble in water. However, they may also be partially crosslinked, for example, with diluted formaldehyde, during their precipitation into aqueous aliphatic alcohols.

All above mentioned hydrogels serve only as examples by which the invention is not limited by any means.

The methods and equipment common in the processing of rubber mixes, calendering in particular, can be used for mixing of non-swollen powdered hydrogels with silicone rubber. Vulcanization may be performed, for example, with the 50% paste of bis(2,4-dichlorobenzoyl) peroxide in silicon oil. Further suitable non-swelling filler, e.g. a finely powdered silica, can be added into mixes for the additional reinforcement.

The following examples illustrate the subject of the invention without limiting it by any means.

EXAMPLE 1

Pure 2-hydroxyethyl methacrylate containing 2% of ethylene dimethacrylate was dissolved in toluene to a 15% solution, 0.3 wt.% of 2,2-azobis(butyronitrile) related to 2-hydroxyethyl methacrylate was added and the solution was heated under reflux and stirring for 2 hours. The pasty product was filtered, dried and the resulting powdered poly-HEMA with the specific surface area 8 $m^2/g$ (determined by the BET method) was mixed with the commercial silicone rubber, having the viscosity average molecular weight about 500,000, on a two-roll mix. The mixes containing 20, 50 and 100 wt. parts of powdered poly-HEMA on 100 wt. parts of rubber were prepared and mixed with 1.2 wt. parts of the paste from equal amounts of bis(2,4-dichlorobenzoyl) peroxide and silicone oil on 100 wt. parts of rubber. Sheets 1 mm thick were press-moulded from these mixes at 110° C. for 15 minutes.

The equilibrium water swell was in the swollen composites, containing 20, 50 and 100 parts of powdered poly-HEMA per 100 parts of rubber, 16, 20 and 32 volume percent, respectively. Because the volume increase caused by equilibrium swelling with water is in poly-HEMA 68% at normal temperature and in the unfilled silicone rubber vulcanizate 0.9%, the swelling of the composite containing 20 parts poly-HEMA/100 parts rubber should be 9.8%, but the real increase is 16%. The similar effect, but less pronounced, is in composites containing 50 and 100 parts of powdered poly-HEMA/100 parts rubber. The composite containing 50 parts of the powdered hydrogel filler per 100 parts rubber had the following mechanical properties (the values in parentheses relate to the gum silicone rubber vulcanizate: tensile strength 1.62 MPa (0.3 MPa), tensile stress at 100% elongation 1.4 MPa (0.27 MPa), elongation at break 250% (130%). The water-swollen composite had the following mechanical properties: tensile strength 0.42 MPa, tensile strength at 100% elongation 0.17 MPa, elongation at break 350%.

The hydrophilic filler improves the modulus and tear strength of silicone rubber in the dry state in a dependence on the concentration of filler particles and on their surface area. These values decrease by swelling, but even at equilibrium swelling are higher than the corresponding values for the unfilled silicone rubber vulcanizate, in spite of a substantially reduced content of rubber in the composite due to the swollen filler, the strength of which approaches to zero. At the same time, the elongation at break increases.

If the composite according to the invention is heated to temperature above approx. 110° C., drawn and then cooled to ambient temperature in the elongated state, a relatively high permanent deformation results which is reversible and can be eliminated either by swelling or by repeated heating above 100° C. Table shows this effect for the content of poly-HEMA filler 20 and 50 parts/100 parts rubber.

|  | Elongation of sample | |
|---|---|---|
|  | Before swelling | After swelling with water |
| Silicone rubber with 20 parts poly-HEMA/100 parts rubber | 45% | 0% |
| Silicone rubber with 50 parts poly-HEMA/100 parts rubber | 85% | 5% |

The filled rubber was drawn by 100% of the original length at 135° C. and cooled. From the measurements ensues that the hydrogel filler turns the original unfilled elastomer to the material with thermoplastic properties. True elastomers exhibit such reversible plastic deformation first at much lower temperature.

EXAMPLE 2

2-Hydroxyethyl methacrylate (HEMA), ester of methacrylic acid and 2,2'-oxydiethanol, and ethylene dimethacrylate were mixed in the wt. ratio 49:49:2 and the resulting monomer mixture was dissolved in toluene to the concentration 15 wt.-%. 2,2'-Azobis(isobutyronitrile) was added to this solution in the amount 0.3 wt.-% related to the monomers. The solution was heated under reflux and stirring for 2 hours. A pasty product was filtered, washed three times and dried. The prepared powdery copolymer had the specific surface area 5.6 $m^2/g$ (determined by the BET method). $\alpha$-Hydroxy-$\omega$-hydrogen-poly(dimethylsiloxane) with the number average molecular weight 2,000 was mixed with methyltriacetoxysilane as a crosslinking agent in the wt. ratio 96:4. After 2 minutes, the powdered copolymer prepared in the above described way was mixed with this liquid mix in the ratio 1 wt. part of the powdered copolymer with 2 wt. parts of the liquid mix. The mixture was pressed in a mould where it reacted for 12 hours at ambient temperature. The prepared moulding from the elastomer silicone composite containing 29.7 wt-% of water after equilibrium swelling in water.

EXAMPLE 3

A moulding was prepared from the elastomeric silicone composite in the same way as described in example 2, with the distinction that a mixture of 3 wt. parts of ethyl silicate and 1 wt. part of dibutyl tin dilaurate was used instead of methyltriacetoxysilane as the crosslinking agent. The weight ratio of the crosslinking agent to $\alpha$-hydroxy-$\omega$-hydrogen-poly(dimethylsiloxane) was the same as in example 2. The resulting elastomeric silicone composite contained 31.2 wt.-% of water after swelling in water in equilibrium.

EXAMPLE 4

A multiblock copolymer of acrylonitrile with acrylamide and acrylic acid was obtained by alkaline hydrolysis of polyacrylonitrile, which was carried out with 2 wt.% of sodium hydroxide on polyacrylonitrile dissolved in the 65% aqueous solution of sodium sulfocyanide. The multiblock copolymer was precipitated in a pasty form by pouring the reaction solution into 60% aqueous methanol under cooling and stirring. The paste of copolymer, which was insoluble in methanol and absorbed 65% of water, was filtered and washed with methanol until the filtrate did not give the reaction of sulfocyanide. The hydrogel was dried and ground to powder which was blended with silicone rubber on a two-roll mix and vulcanized according to example 1. The obtained composite had similar properties as the product in example 1.

EXAMPLE 5

Silicone composites containing powdered hydrogel filler were prepared by the procedure described in example 1 with the distinction that the precipitation polymerization was carried out with a 15% toluene solution of monomers containing 86.1% of 2-hydroxyethyl methacrylate, 1.7% of ethylene dimethacrylate, and 8.5% of methacrylic acid. The equilibrium swelling of the composite, prepared in this way and containing 50 parts of powdered hydrogel per 100 parts rubber, in water and aqueous solutions depended on pH. Thus, the equilibrium swelling in the phosphate buffer with pH 5.2 amounted to 19%. whereas the swelling of the same composite in the buffer with pH 7.3 was 82.5%. The composite had tensile strength 0.87 MPa and elongation at break 70% in the non-swollen state. The composite swollen in the buffer with pH 5.2 to equilibrium had tensile strength 0.16 MPa, tensile stress at 100% elongation 0.12 MPa and elongation at break 140%.

EXAMPLE 6

The cylindric moulding from crosslinked poly(2-hydroxyethyl methacrylate) of 50 mm diameter and 80 mm length was prepared by the bulk polymerization of 2-hydroxyethyl methacrylate containing 0.6% of ethylene dimethacrylate and mechanically disintegrated to irregular particles with the maximum size not exceeding 10 mm. The particles were ground in an impact mill of 180 mm diameter and rotation speed 9000 r.p.m. for 3 min. The resulting finely ground hydrogel filler (33.3 wt.-%) was mixed with 65.9 wt.-% of silicone rubber having the average molecular weight about 500.000 and 0.8 wt.-% of a paste containing the same amounts of bis(2,4-dichlorobenzoyl) peroxide and silicon oil. Sheets 1 mm thick were pressed from the mix at 110° C. for 15 min. The obtained silicone composite has the volume swell in water 16%, tensile strength 0.23 MPa and elongation at break 30% in the non-swollen state. The water-swollen composite had tensile strength 0.18 MPa and elongation at break 90%.

EXAMPLE 7

A spongy polymer was obtained in the form of 2 mm thick sheets by polymerization of the mixture containing 40 wt.-% of 2-hydroxyethyl methacrylate, 0.2 wt.-% of ethylene dimethacrylate and 60 wt.-% of water. The sheets of spongy hydrogel were cut to smaller parts of size about 10×10 mm and dried to a hard and brittle polymer. The dried polymer was crushed to particles of 0.3–1 mm size which were further ground in a porcelain ball mill for 24 hours. The finely ground hydrogel filler (33.3 wt.-%) was mixed with 65.9 wt.-% of silicone rubber having the average molecular weight about 500.000 and with 0.8 wt.-% of a paste from the same amounts of bis(2,4-dichlorobenzoyl) peroxide and silicone oil. Sheets with thickness 1 mm were press-moulded from the mix at 110° C. for 15 min. The obtained silicon composite had volume swell in water 18.3%, tensile strength 0.45 MPa and elongation at break 180%.

EXAMPLE 8

The powdered hydrogel filler was prepared by the procedure described in example 1 and was used in the amount of 33.3 wt.-% for the preparation of a mix further containing 55.1 wt.-% of silicone rubber with the average molecular weight about 500,000, 11.2 wt.-% of fumed silica filler (Aerosil 130, Degussa), and 0.7 wt.-% of a paste from equal amounts of bis(2,4-dichlorobenzoyl) peroxide and silicone oil. Sheets with thickness 1 mm were press-moulded from this mix at 110° C. for 15 min. The obtained silicone composite had the volume swell in water 17% and tensile strength 2.6 MPa.

We claim:

1. A hydrophilic silicone composite comprising a crosslinked silicone polymer which forms a continuous matrix, having incorporated therein a powdered hydrogel filler comprising particles having a particle size from about $10^{-6}$ to $10^{-1}$ mm, said hydrogel being selected from the group consisting of
    cross-linked polymers and copolymers of glycol monomethacrylates, polyol monomethacrylates, dihydroxyester monomethacrylates, acrylamide, methacrylamide, N-substituted acrylamide, N-substituted methacrylamide, N,N-disubstituted acrylamide, N,N-disubstituted methacrylamide, and
    multiblock copolymers of acrylonitrile with acrylamide and/or acrylic acid;
said powdered hydrogel filler being present in an amount from about 10 to about 150 weight parts per 100 weight parts of silicone polymer.

2. Method for producing the composite according to claim 1, wherein the powdered filler is mixed into a non-crosslinked silicone rubber which is, after shaping crosslinked by the known procedure of silicone rubber vulcanization at temperature ranging from 15° to 200° C.

3. The composite of claim 1 wherein the hydrogel is selected from the group consisting of poly(2-hydroxyethyl methacrylate), a multiblock copolymer of acrylonitrile with acrylamide and/or acrylic acid, and a cross-linked polymer the 2,2'-oxydiethanol ester of methacrylic acid.

* * * * *